United States Patent [19]

Jauregui

[11] Patent Number: 4,795,459

[45] Date of Patent: Jan. 3, 1989

[54] IMPLANTABLE PROSTHETIC DEVICE WITH LECTIN LINKED ENDOTHELIAL CELLS

[75] Inventor: Hugo O. Jauregui, Providence, R.I.

[73] Assignee: Rhode Island Hospital, Providence, R.I.

[21] Appl. No.: 51,500

[22] Filed: May 18, 1987

[51] Int. Cl.$^4$ ............................................. A61F 2/06
[52] U.S. Cl. ........................................ 623/1; 623/11;
623/12; 623/66; 435/1; 435/180; 436/827
[58] Field of Search ............ 128/DIG. 3; 435/1, 240,
435/180, 182; 436/827; 623/1, 2, 11, 12, 66

[56] References Cited

U.S. PATENT DOCUMENTS

| | | | |
|---|---|---|---|
| Re. 31,712 | 10/1984 | Giese | 604/4 |
| 3,636,956 | 1/1972 | Schneider | 128/335.5 |
| 4,035,316 | 7/1977 | Yen et al. | 436/827 |
| 4,355,426 | 10/1982 | MacGregor | 623/1 |
| 4,546,500 | 10/1985 | Bell | 623/1 |
| 4,614,517 | 9/1986 | Ruoslahti et al. | 623/1 |

FOREIGN PATENT DOCUMENTS 3422639 12/1985 Fed. Rep. of Germany .......... 623/1

OTHER PUBLICATIONS

Jarrell et al., "Use of an Endothelial Monolayer on a Vascular Graft Prior to Implantation", *Ann. Surg.*, Jun. 1986, pp. 671-678.

Hatten et al., "Adhesive Specificity of Developing Cerebral Cells on Lectin Substrata", *Developmental Biology*, vol. 87, 1981, pp. 102-113.

Primary Examiner—Richard J. Apley
Assistant Examiner—Paul B. Prebilic

[57] ABSTRACT

An implantable prosthetic device made of biocompatible polymer and having a substantially continuous layer of autologus living cells attached via oligosaccharide-lectin recognition linkages.

11 Claims, 2 Drawing Sheets

IMPLANTABLE PROSTHETIC DEVICE WITH LECTIN LINKED ENDOTHELIAL CELLS

FIELD OF THE INVENTION

The invention relates to implantable prosthetic devices.

BACKGROUND OF THE INVENTION

It may be desirable to provide a layer of cells on a surface of an implanted prosthetic device. E.g., implantable cardiovascular devices, e.g., vascular prostheses, artificial hearts, and heart valves, should support rapid endothelial coverage and allow a maximal rate of endothelial migration on their surfaces, because incomplete endothelialization of such surfaces may eventually lead to thrombo-embolic episodes and ultimately to failure of some of these prosthetic devices.

Endothelial cells have been seeded on prosthetic devices to promote endothelialization, as is discussed in Bourke, M. et al., "Endothelial cell harvest for seeding vascular prostheses: The influence of technique on cell function, viability, and number," *J. Vascular Surgery*, Vol. 4, No. 3, Sept, 1986, pp. 257-263. Jarrell et al., "Use of Endothelial Monolayer on a Vascular Graft Prior to Implantation", *Ann. Surg.*, June 1986, pp. 671-678, and Jarrell et al., "Use of Freshly Isolated Capillary Endothelial Cells for the Immediate Establishment of a Monolayer on a Vascular Graft at Surgery", *Surgery*, Vol. 100, No. 2, August 1986, pp. 392-399, describe the desirability of establishment of an intact endothelium at or near time of implantation, and seeding of endothelial cells on a woven Dacron surface pretreated with platelet rich plasma or human amnion. Fasol, R. et al., "Experimental In Vitro Cultivation of Human Endothelial Cells on Artificial Surfaces", *Trans. Am. Soc. Artif. Intern. Organs*, Vol. XXXI, 1985, pp. 276-283, discloses treating PTFE with fibronectin to promote growth of an endothelial layer thereon.

SUMMARY OF THE INVENTION

In one aspect the invention features an implantable prosthetic device made of biocompatible polymer and having living cells attached via oligosaccharide lectin recognition linkage.

In preferred embodiments the cells are autologous endothelial cells; the prosthetic device is used in the patient's cardiovascular system; the lectin recognizes α-L-fucose (most preferably the lectin is Ulex Europaeus I agglutinin or wheat germ agglutinin); the lectins are bound to the polymer by the carbodiimide or glutaraldehyde methods; and the polymer is Teflon, Dacron, polyurethane, or a polymer of a compound of the Krebs cycle, and the surfaces of the polymer are processed to provide COOH or $NH_2$ groups for covalently attaching the lectins.

In another aspect the invention features a method of implanting a prosthetic device comprising removing cells from a patient, attaching them to a polymer via oligosaccharide lectin recognition linkages, growing a cell layer on the surface, and implanting the device in the patient. An advantage of the invention is that it permits high density seeding, which results in quick growth of endothelial cells.

Other advantages and features of the invention are within the scope of the following description of the preferred embodiment and from the claim.

DESCRIPTION OF THE PREFERRED EMBODIMENTS

The preferred embodiments will now be described.

DRAWINGS

STRUCTURE

Figure 1:
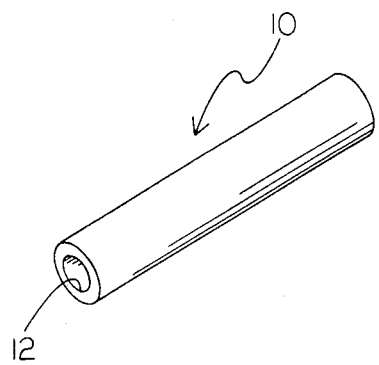
FIG. 1 is a diagrammatic representation of an implantable artificial blood vessel.

Referring to FIG. 1, there is shown artificial blood vessel 10 (e.g., a small coronary artery) for implanting in a patient to convey blood as part of the patient's cardiovascular system. It is made of biocompatible polymer and a layer of endothelial cells (not shown in FIG. 1) providing inner surface 12 defining a flow passage for blood.

Figure 2:
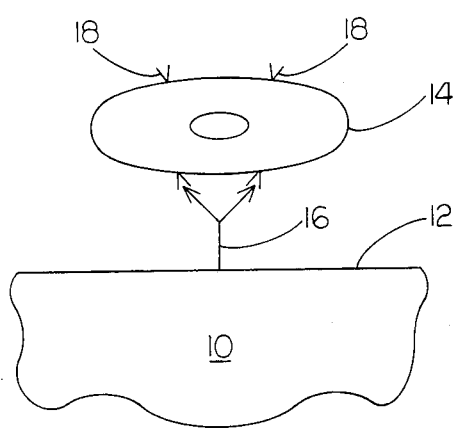
FIG. 2 is a diagrammatic representation of a cell attached to a biocompatible polymer according to the invention.

In FIG. 2 there is shown endothelial cell (EC) 14 attached to vessel 10 by a lectin 16, which is covalently bound to the biocompatible polymer of vessel 10 and recognize specific oligosaccharides 18 on cell 14.

MANUFACTURE AND USE

Vessel 10 is made from a biocompatible polyurethane tube, the inner surface of which has been treated by corona discharge to provide hydroxyl groups, which are then used to provide carboxy and/or amino groups, according to well known techniques (Curtis, A. S. G., et al., "Substrate Hydroxylation and Cell Adhesion", *J. Cell Science*, Vol. 86, 1986, pp. 9-24, Schnabel, W., *Polymer Degradation*, (Munich, 1981)).

Ulex Europaeus I lectins are covalently bonded to the interior surface of the tube at the carboxy and amino groups using the carbodiimide method described in Hatten, M. E. and Francois, A. M., "Adhesive Specificity of Developing Cerebellar Cells on Lectin Substrata," *Develop. Biol.*, Vol. 87, 1981, pp. 102-113, which is hereby incorporated by reference. (See discussion in part III.A. below.)

Endothelial cells are removed from the patient to receive the device between one and four weeks before the implantation. The cells are attached at high density numbers using sugar residues (oligosaccharides) on their surfaces to the lectins on the inner surface of the tube by the method described below (see discussion in part III.B.), and a monolayer of endothelial cells grows over the course of several days (long term cell culture). After the layer has grown, the device is implanted. An autologous endothelial monolayer thus is formed prior to implantation, completely lines the vascular lumen, and desirably avoids thrombosis for the implanted cardiovascular device.

The experiments described below were performed to evaluate (Procedures, parts I, II below) the abilities of different lectins, having various carbohydrate specificities, to recognize sugars present on human endothelial cells (in order to identify sugars present on a variety of cells and thus identify a lectin or lectins that could be used with a variety of endothelial cells) and to evaluate (Procedures, part III below) the ability of human umbilical vein endothelial cells (UVEC) to attach to and grow on lectins covalently bound to polymers. Fifteen lectins were first evaluated with endothelial cells from different human vessels: umbilical and saphenous veins, large and medium arteries (e.g, aorta, coronary, liliac, umbilical), and small arterioles from adrenal gland and liver. The fifteen lectins evaluated are listed below in Table I along with their carbohydrate specificities.

TABLE I

| LECTIN | CARBOHYDRATE SPECIFICITY |
|---|---|
| Ricinus communis agglutinin (RCA I) | β-D-galactose, α-D-galactose |
| Wheat germ agglutinin (WGA) | NAc-neuraminic acid, β-NAc glucosamine |
| Pisum sativum agglutinin (PSA) | α-D-mannose, α-D-glucose |
| Lens culinaris agglutinin (LCA) | α-D-mannose, α-D-glucose |
| Phaseolus vulgaris agglutinin (PVA) | β-D-NAc-glucose-galactose, β-D-mannose |
| Canavalia ensiformis Concanavalin A (Con A) | α-D-mannose, α-D-glucose, α-NAc-glucosamine |
| Ulex Europaeus agglutinin I (Ulex I) | α-L-fucose |
| Ulex Europaeus agglutinin II (Ulex II) | (D-glucose NAc)$_2$ |
| Sophora japonica agglutinin (SJA) | NAc-β-D-galactosamine |
| Phaseolus vulgaris leucocyte agglutinin (PVLA) | unknown |
| Succinylated wheat germ agglutinin (SWGA) | NAc-neuraminic acid |
| Bandeirea simplicifolia agglutinin (BSLA) | α-D-galactose |
| Dolichos biflorus agglutinin (DBA) | α-D-galactosamine |
| Peanut agglutinin | β-D-galactose-(1,3)-NAc β-D-galactose |
| Soybean agglutinin | galactose NAc-D-galactosamine. |

After this evaluation, the lectins that bound onto cell surfaces of endothelial cells at high levels, and two additional lectins, Cytisus sessilifolius agglutinin (CSA) and Lotus tetragonolobus agglutinin (LTA), which have α-L-fucose specificity, were evaluated as substrates for human umbilical vein endothelial cell attachment in polystyrene dishes, which already have carboxy groups, and thus did not need to be modified to provide these groups, as with the polyurethane used in the prosthetic device described above.

PROCEDURE

I. Sugar residue characterization of endothelial cells from different tissues

1. Fixation: Tissue samples approximately 3×2 mm were fixed for 24 hours in a modified Karnovsky solution containing 4% paraformaldehyde and 0.5% glutaraldehyde in 0.15 M sodium cacodylate buffer (pH 7.4). The specimens were rinsed with FTA buffer, successively transferred to FTA buffer containing 10%, 18%, 25% sucrose (24 hours each), followed by immersion in a solution of 10% glycerol and 25% sucrose in FTA buffer for one half hour.

The samples were then embedded in a cryoprotective embedding medium (OCT), frozen in Freon 22, and sectioned in a cryomicrotome.

2. Lectin staining: Commercially available biotin conjugated lectins were purchased from E-Y Laboratories (San Mateo, Calif.) and Vector Laboratories (Burlingame, Calif.).

The following procedure represents a modification of the protocol used by McMillan, P. N., et al., "Light and electron microscope analysis of lectin binding to adult rat liver in situ." Lab Invest., 50(4), 1984, pp. 408–420. Cryotome sections were immersed in absolute methanol containing 0.3% hydrogen peroxide and 0.074% hydrochloric acid for thirty minutes at ambient temperature to eliminate endogenous peroxidase activity. Subsequently, the sections were washed in FTA buffer. Each section was treated and incubated for one hour with one of fifteen biotinylated lectins on Table I, except for the control slides for which this step was omitted. The concentration of lectins applied was 2 μg/ml in FTA buffer (except for Ulex I which was 6 μg/ml). Subsequently the sections were washed in FTA buffer and incubated for 45 minutes at ambient temperature with an avidin-biotin peroxidase mixture (ABC) prepared according to instructions supplied with a Vecta Stain ABC kit (Vector Laboratories, Burlingame, Calif.). The final reaction product was developed by immersing the sections in a solution of 0.01% hydrogen peroxide and 0.05% diaminobenzidine tetrahydrochloride (DAB) in FTA buffer for 5–10 minutes. Finally, washed sections, dehydrated with ethanol and methanol, and counterstained with methyl green (1% in absolute methanol), were cleared in xylene, and mounted for examination and evaluation by light microscopy.

II. Cytophotometry of Lectin Binding onto Umbilical Endothelial Cells

A. Isolation and Culture of UVEC

Human umbilical cords were severed from the placenta soon after birth and placed in a sterile container filled with cord buffer (137 mM NaCl, 4 mM KCl, 10 mM HEPES, 11 mM dextrose, pH 7.4), supplemented with Fungizone (0.05 mg–100 ml and gentamicin (0.05 mg/100 ml). EC were harvested from the umbilical vein by the collagenase separation method of Jaffe E. A., et al., "Culture of human endothelial cells derived from umbilical veins", J. Clinical Invest. 52, 1973, page 2745, et seq. The yield of this procedure was in the range of 1–1.5×10$^6$ cells per cord. The identity of EC was verified by morphological (light and electron microscopy, including the demonstration of coldestone pattern and Weibel Palade bodies) and immunological (VIII Antigen) methods. The UVEC suspension was divided equally among four chambers of Lab-Tek 4-chamber glass slides (Miles Scientific, Naperville, Ill.) precoated with fibronectin. UVEC were cultured in Tissue Culture media 199 (Gibco Laboratories, Grand Island, N.Y.) containing 10% fetal bovine serum (Gibco Laboratories, Grand Island, N.Y.) penicillin/streptomycin (100 U/ml), L-glutamine (Gibco Laboratories, Grand Island, N.Y.), heparin (1000 U/ml), and endothelial cell growth factor (75 μg/ml) (Collaborative Research, Lexington, Mass.). The chamber slides were incubated (at 37°, 5% CO$_2$ for 48 hours before being processed for lectin binding experiments.

1. Fixation: Both freshly-isolated and 48 hour cultured EC were fed serum-free media 24 hours prior to their processing to eliminate any serum factor interference with the lectin binding procedure. The EC were fixed for one half hour with 0.5% glutaraldehyde in 0.15 M sodium cacodylate solution.

2. Lectin staining: The aforementioned staining procedure was followed with the following modifications.

After the lectin staining step, the cells were not dehydrated, but were post fixed for one hour in 1% osmium tetroxide contained in 0.1 M sodium cacodylate buffer (pH 7.4). After immersion overnight in 0.1M sodium cacodylate buffer, the cells were embedded directly in chambers with Spurr's low viscosity epoxy resin (Ladd Research Industries, Burlington, VT). Semithin sections of EC (0.5 μm as determined by optical birefringence) were used for cytophotometry measurements.

3. Quantification method: A cytophotometric quantitation of lectin binding was performed by means of a Vickers M85/86 Scanning Microdensitometer (Vickers Corp., London, England). The sections were viewed at a magnification of 970× with wave length, beam spot size, and gating mask size of 350 nm, 0.2 μm, and 6.5 μm, respectively. Individual measurements were made in the following manner:

a. The circular gating mask was precisely centered over the plasma membrane of an individual EC with one half of the circle overlying the extracellular space. The beam spot was then positioned outside the cell, but within the gating mask and the density meter was set to read zero.

b. An optical density reading was made in the "scan" mode. In "scan" the beam spot repeatedly traverses the selected field for a specified time interval (0.06 seconds for X-axis and 5 seconds for Y axis) making 10,000 optical density measurements per second. The sum of these measurements is displayed in results in FIGS. 3 and 4 as an integral total in "machine units".

c. The gating mask (with enclosed beam spot) was moved completely into the cytoplasmic compartment to a region immediately adjacent to the portion of the plasmalemma scanned in step b.

d. A second reading was performed in "scan" mode. One half of this value was subtracted from measurements obtained in step b, and the difference was recorded as the final measurement.

e. Portions of the plasma membrane to be measured were selected randomly with the reservation that ragged areas with surface blebs were excluded.

f. The values plotted on the graphs (FIGS. 3 and 4) represent averages (±standard deviations) of 20 measurements for each lectin. The values of lectin intensity plotted were normalized between 0 and 100%.

III. Biochemical Assay of Cell Attachment

An adhesion assay that allowed selective measurement of cell adhesion mediated by lectin was used. EC attachment to lectin substrates was measured by quantifying the protein content of the attached cells. Total cell protein content was assessed by a modification of Ponceau-S micromethod (Hayner N. T., et al., "Ponceau S: a sensitive method for protein determination in freshly isolated and cultured cells." *J. Tissue Cult. Methods* 7(2), 1982, pp. 77–80. Protein values for culture media were corrected for by eliminating the fetal bovine serum and ECGF from the media. The percentage of protein attached was calculated by comparing readings of unknown values from a standard protein curve. The following formula was used for this calculation:

% Protein attached = AP/TP × 100

AP = attached cell protein (mg)
TP = total protein seeded (mg) (as initial inoculated cells)

A. Preparation of Lectin Substrates (Immobilization of Lectins).

Nine selected lectins were coupled to 35 mm polystyrene tissue culture dishes by a modification of the method of Halten M. E., and Francois, A. M., "Adhesive specificity of developing cerebellar cells on lectin substrates", *Develop. Biol.*: 87, 1981, pp. 102–113. Uncoated polystyrene dishes were used as a control throughout these attachment experiments. In brief, lectin (10 μg/ml) was added to 10 ml 0.15 M NaCl solution of carbodiimide [1-cyclohexyl-3-(2-morpholinoethyl)-carbodiimide-metho p-toluene sulfonate] (5 mg/ml, Aldrich Chemical Co., Milwaukee, Wis.). This mixture was used to coat the culture dishes (1 ml per dish, room temperature, 30 minutes), referred to as lectin plates.

B. Preparation of Endothelial Cells and Assay Method.

A 1 ml aliguot of the freshly isolated UVEC suspension (250,000–500,000 cells/ml) was used to coat each lectin plate, and the plates were incubated at 37° C., 5% $CO_2$ for 90 minutes (except for the time study experiments). The supernatant containing the non-attached EC (pellets) was sedimented twice, at 160×g for periods of fifteen minutes and ten minutes, with a 5 minute sitting period between sedimentations. The supernatant was discarded, and 10 ml Ponceau-S-TCA (trichloroacetic acid) was added to tubes and left to react for thirty minutes.

The attached EC on the lectin-coated plates were also treated with Ponceau-S-TCA in the same manner. The attached EC were scraped off the plates and, along with the non attached cells, were sedimented at 1000×g for thirty minutes to pellet any lipid material. The Ponceau-S solution was aspirated, and 10 ml sodium hydroxide (8 g/L, 0.2 N) was added to produce a violet color reaction. Optical densities were measured colorimetrically with Ministat S at OD 546 (Chemistry Analyzer, Bickinetix).

RESULTS

I. Light Microscopy of Lectin Binding

The fifteen ABC labeled lectins exhibited various degrees of binding to the endothelium of in situ human tissues as set forth below in Table II. BSLA, DBA, SJA, peanut agglutinin and soybean agglutinin completely failed to react with almost any endothelial structures. In contrast, RCA I, WGA, Con A, LCA, Ulex I reacted with EC regardless of the vessel size and tissue origin of arterial or venous source of the vessels, indicating that these lectins would perform well in attaching endothelial cells to polymers of prosthetic devices to which the lectins were covalently bound.

TABLE II

Summary of Light Microscopy Evaluation of Intact (in situ) Endothelial Cell Lectin Staining (N = 4)

| | LARGE VEINS | | LARGE AND MEDIUM ARTERIES | | | | SMALL ARTERIES | |
|---|---|---|---|---|---|---|---|---|
| | Umbilical | Saphenous | Aorta | Coronary | Iliac | Umbilical | Adrenal | Liver |
| 1. BSLA | 0 | 0 | 0 | 0 | 0 | 0 | 0 | 0 |
| 2. Con A | 3 | 3 | 3 | 2 | 2 | 3 | 2 | 3 |
| 3. DBA | 0 | 0 | 0 | 0 | 0 | 0 | 0 | 0 |

TABLE II-continued

Summary of Light Microscopy Evaluation of Intact (in situ) Endothelial Cell Lectin Staining (N = 4)

| | LARGE VEINS | | LARGE AND MEDIUM ARTERIES | | | | SMALL ARTERIES | |
|---|---|---|---|---|---|---|---|---|
| | Umbilical | Saphenous | Aorta | Coronary | Iliac | Umbilical | Adrenal | Liver |
| 4. LCA | 2 | 3 | 3 | 2 | 3 | 2 | 3 | 2 |
| 5. PSA | 1 | 2 | 2 | 2 | 2 | 2 | 1 | 2 |
| 6. PVA | 2 | 2 | 2 | 1 | 2 | 2 | 2 | 1 |
| 7. Peanut agglut. | 0 | 0 | 0 | 0 | 0 | 0 | 0 | 0 |
| 8. RCA I | 3+ | 3+ | 3 | 2 | 3+ | 3 | 2 | 3 |
| 9. SJA | 0 | 0 | 0 | 1 | 1 | 0 | 0 | 0 |
| 10. Soybean agglut. | 0 | 0 | 0 | 1 | 1 | 0 | 0 | 0 |
| 11. Ulex I | 3 | 1 | 2 | 2 | 1 | 3 | 1 | 2 |
| 12. Ulex II | 2 | 1 | 1 | 2 | 1 | 1 | 1 | 0 |
| 13. WGA | 3+ | 3+ | 2 | 2 | 2 | 3+ | 2 | 3+ |
| 14. PVLA | 2 | 1 | 2· | 1 | 2 | 2 | 2 | 1 |
| 15. SWGA | 2 | 2 | 1 | 2 | 1 | 2 | 2 | 1 |

Results are expressed as intensity of staining as evaluated by light microscopy. Grading performed on the following scale: 0 = no staining, 1 = faint, 2 = moderate, 3 = intense, 3+ = very intense.
Values given are averages derived from four experiments in which duplicate sections were scored for each lectin.

II. Cytophotometry of Lectin Binding

Ten of the fifteen ABC labeled lectins which stained positively the endothelium of intact human tissues (Table II), plus two additional lectins (LTA and CSA) with the same nominal specificity (α-L-fucose) as Ulex I, were selected for quantitative evaluations. Lectin binding was homogeneously distributed around the perimeter of freshly isolated and 48-hour cultured EC.

Figure 3:
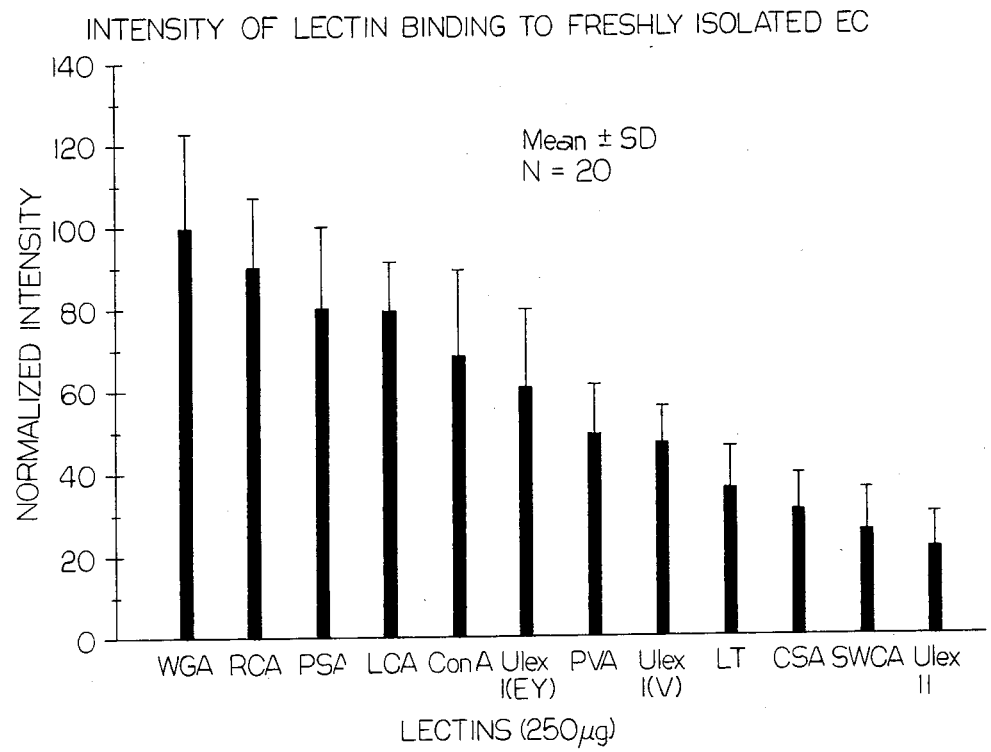
FIG. 3 is a graph of intensity of lectin binding to freshly isolated endothelial cells for plural lectins.
Figure 4:
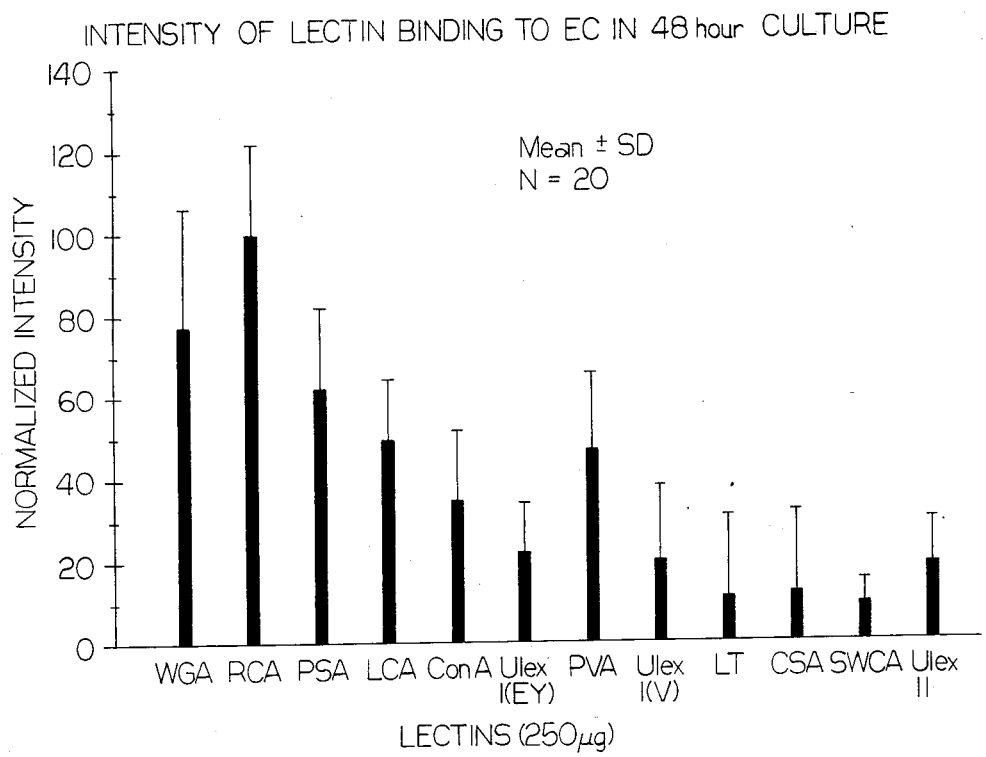
FIG. 4 is a graph of lectin binding to endothelial cells in 48 hour culture for plural lectins.

Measurements were made randomly with 20 different EC for each lectin. The results of the lectin binding intensity studies of freshly isolated vs. 48 hour cultured EC are illustrated in FIGS. 3 and 4. Although UVEC maintain the same sugar specificity up to 48 hours in culture, the intensity of binding is reduced when compared to that of freshly isolated EC. RCA was exceptional in being the only lectin that exhibited an elevation in binding as the cells were cultured. Ulex I, CSA, and LTA show the most striking decrease in their binding intensity when allowed to react with cultured EC. The intensity of binding of these α-L-fucose specific lectins decreases threefold in cultured EC, compared to freshly isolated EC.

III. Biochemical Assay of Lectin Attachment

Figure 5:
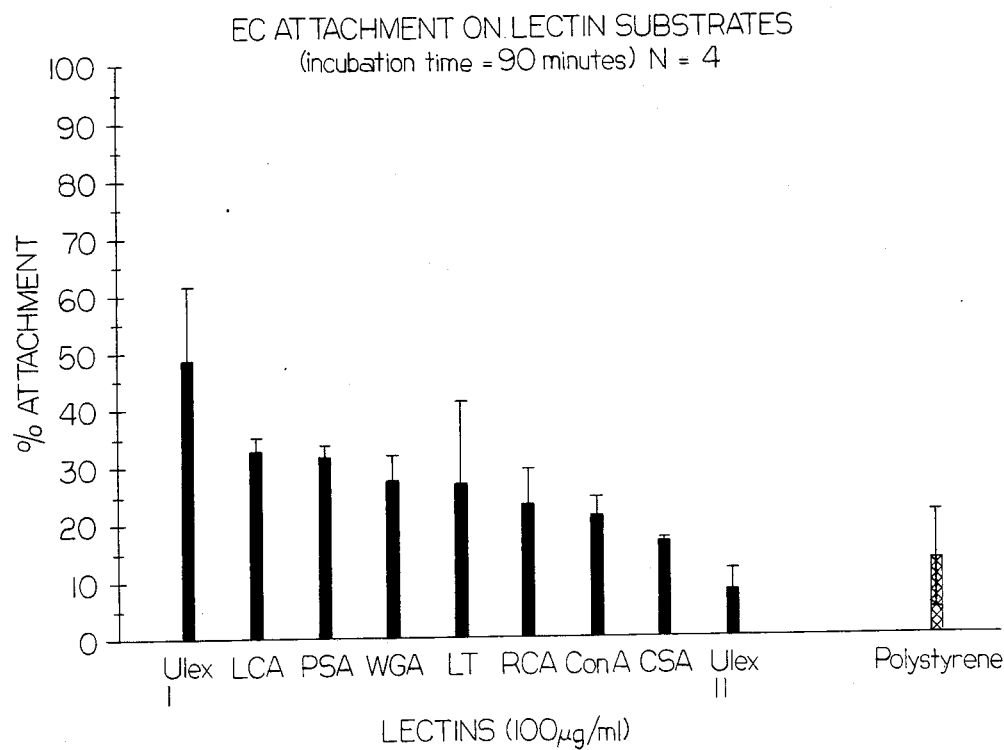
FIG. 5 is a graph of endothelial cell attachment on lectin substrates bound to polystyrene for plural lectins.

The results of the attachment studies indicate that freshly isolated human UVEC have different adhesive specificities on lectins of different carbohydrate selectivity (FIG. 5). On Ulex I derivative substrate, the UVEC showed a maximum attachment within ninety minutes of incubation time (50% attachment), compared to the eight other lectin-derivative substrates. LCA, PSA, WGA, RCA, LTA lectins showed 30% attachment in the same period of time as Ulex I, and the percentage of attachment was below 20% for Con A, CSA, and Ulex II lectins in substrates and for the control polystyrene plates. Although Ulex I, CSA, and LTA lectins share the same nominal specificity for α-L-fuctose sugar residue, their UVEC attachment profiles are quite different Ulex I lectin substrates exhibit the maximum degree of attachment for UVEC (50%), whereas attachment efficacy of CSA lectin substrates falls in the lower range of the UVEC lectin attachment spectrum (20% attachment).

The results of both cytophotometric and biochemical studies show that the lectin binding intensity of freshly isolated UVEC glycocalyces does not parallel the freshly isolated UVEC attachment profile of these lectins. RCA and WGA lectins show the maximum binding intensity to UVEC, whereas Ulex I seems to be the superior lectin for UVEC attachment.

Based on the results, Ulex I is the preferred lectin for use in attaching endothelial cells via lectin oligosaccharide recognition linkage to biocompatible polymers of prosthetic devices.

OTHER EMBODIMENTS

Figure 2A:
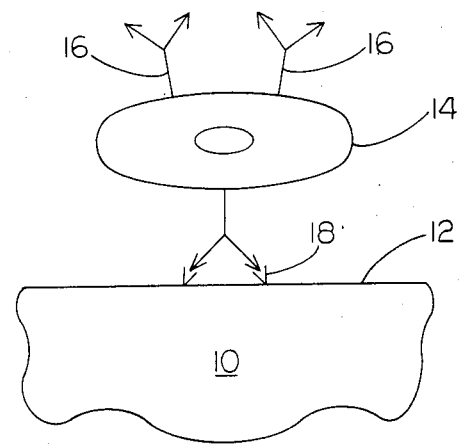
FIG. 2A is a diagrammatic representation showing an alternative mechanism of a cell attached to a biocompatible polymer.

Other embodiments of the invention are within the scope of the following claims. For example, the invention can be employed in prosthetic devices other than those used in the cardiovascular system and with cells other than endothelial cells, provided they have surface oligosaccharides that can be recognized by lectins or carry lectins themselves. Similarly, lectins other than those identified above can be used depending upon the particular cell and the oligosaccharides on its surface The lectins could be covalently bound to the polymer by a method other than the carbodiimide methods, e.g., the glutaraldehyde method. Also, if the cell carries a lectin, an oligosaccharide could be covalently bound to the polymer, as is described in FIG. 2A. Finally other biocompatible polymers such as Dacron, PTFE or bioresorbable polymers of compounds of the Krebs cycle (e.g., polyglutaric acid) can be used in the prosthetic device.

What is claimed is:

1. An implantable prosthetic device comprising a member that has a shape to perform a cardiovascular prosthetic function when implanted, is made of biocompatible polymer, and has a surface to which a substantially continuous layer of autologous living endothelial cells has been attached via oligosaccharide-lectin recognition linkages.

2. The device of claim 2 wherein said lectin is covalently bound to said polymer, and said oligosaccharide is part of the cell surface of said living cells.

3. The device of claim 2 wherein said lectin is a lectin that recognizes α-L-fucose.

4. The device of claim 2 wherein said lectin is one of the group consisting of Ulex Europaeus agglutinin I, Lens culinaris agglutinin, Pisum sativum agglutinin, wheat germ agglutinin, Lotus tetragonolobus agglutinin, Ricinus communis agglutinin, Concanavalin A, and Cytisus sessilifolius agglutinin.

5. The device of claim 2 wherein said lectin is Ulex Europaeus agglutinin I.

6. The device of claim 2 wherein said lectin is wheat germ agglutinin.

7. The device of claim 1 wherein said member is a tubular vessel that is sufficiently small to function as a coronary artery.

8. The device of claim 1 wherein said polymer is PTFE.

9. The device of claim 1 wherein said polymer is polyurethane.

10. The device of claim 1 wherein said polymer is Dacron.

11. The device of claim 1 wherein said polymer is a bioresorbable polymer of a compound of the Krebs cycle.

* * * * *